United States Patent
Kappelman et al.

Patent Number: 5,391,487
Date of Patent: Feb. 21, 1995

[54] RESTRICTION ENDONUCLEASE SGFI FROM STREPTOMYCES GRISEORUBER

[75] Inventors: James R. Kappelman; Raymond J. Williams; Elizabeth E. Murray; Nadia I. Vesselinova, all of Madison, Wis.

[73] Assignee: Promega Corporation, Madison, Wis.

[21] Appl. No.: 106,934

[22] Filed: Aug. 13, 1993

[51] Int. Cl.⁶ .................. C12P 19/34; C12N 9/22; C12N 1/00
[52] U.S. Cl. .................. 435/91.53; 435/91.1; 435/199; 435/886
[58] Field of Search .................. 435/199, 91.1, 886, 435/91.53

[56] References Cited

U.S. PATENT DOCUMENTS

| | | | |
|---|---|---|---|
| 4,746,609 | 5/1988 | Bolton et al. | 435/91 |
| 4,833,082 | 5/1989 | Yamada et al. | 435/199 |
| 4,960,707 | 10/1990 | Lacks | 435/320 |
| 5,061,628 | 10/1991 | Roberts et al. | 435/199 |
| 5,134,069 | 7/1992 | Kaluza et al. | 435/91 |
| 5,179,016 | 1/1993 | Kotani et al. | 435/199 |
| 5,183,747 | 2/1993 | Kaluza et al. | 435/91 |
| 5,354,669 | 10/1993 | Kaluza et al. | 435/91.53 |

*Primary Examiner*—Marian Knode
*Assistant Examiner*—Jon P. Weber
*Attorney, Agent, or Firm*—Michael, Best & Friedrich

[57] ABSTRACT

A restriction endonuclease is provided. The enzyme, designated SgfI, recognizes the DNA sequence

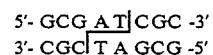

and cleaves the DNA sequence at a position indicated by the arrows and is preferably obtainable from microorganisms of the genus Streptomyces.

13 Claims, No Drawings

RESTRICTION ENDONUCLEASE SGFI FROM *STREPTOMYCES GRISEORUBER*

FIELD OF THE INVENTION

The invention relates to a restriction endonuclease and a method for its isolation and use.

BACKGROUND OF THE INVENTION

Type II restriction endonucleases are endodeoxyribonucleases which are able to recognize and cleave DNA at site-specific sequences. The ability to specifically cleave DNA into discrete fragments is essential for the manipulation of DNA. Type II restriction endonucleases are thus of value for the analysis of DNA molecules.

Although Type II restriction endonucleases are known which are specific for numerous DNA sequences, there is still a need for further type II restriction endonucleases which are specific for DNA sequences that up to now have not been recognized by any of the known restriction endonucleases. Further, the use of restriction endonucleases whose recognition sites contain a large number of base pairs are of particular interest since fewer, larger fragments of DNA are likely to be generated by treatment with such restriction endonucleases. However, most of the restriction endonucleases known recognize a sequence of four to six base pairs, and hence the number of cleavage sites is too great when manipulating DNA, making its analysis difficult in many cases. Thus, there is a demand for restriction endonucleases capable of recognizing a sequence of more than 4 or 6 base pairs.

SUMMARY OF THE INVENTION

The invention provides a type II restriction endonuclease having the recognition sequence

and the cleavage site indicated by the arrows.

It is a feature of the invention to provide a new restriction endonuclease which is able to specifically recognize and cleave a sequence which has previously not been recognized by any such enzyme.

Other features and advantages of the invention will become apparent to those of ordinary skill in the art upon review of the following detailed description and claims.

DETAILED DESCRIPTION OF THE PREFERRED EMBODIMENT

The new restriction endonuclease according to the present invention, hereafter called SgfI, is a Type II restriction endonuclease that is capable of recognizing and cleaving double stranded DNA having the following octanucleotide recognition sequence: 5'-GCGATCGC-3'. SgfI makes staggered cuts along double stranded DNA at the following cleavage sites indicated by the arrows:

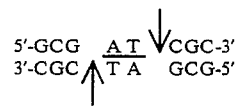

Due to its 8 base pair length, the above-identified recognition sequence is found infrequently along strands of DNA as compared to recognition sequences of fewer base pairs. Thus, SgfI cuts DNA more infrequently. Its ability to be an infrequent cutter makes SgfI a valuable laboratory tool for manipulating DNA. Further, SgfI is complementary to the restriction endonuclease PvuI in that the internal 6 base pairs of the 8 base pair SgfI recognition sequence is identical to the PvuI recognition sequence 5'-CGATCG-3'. PvuI and SgfI also share the same cleavage sites. Therefore, SgfI, when utilized in conjunction with the more frequent cutter PvuI, can be a very effective tool in manipulating DNA.

The restriction endonuclease SgfI of the present invention is preferably obtained from microorganisms of the genus Streptomyces and more specifically, preferably from *Streptomyces griseoruber*. SgfI has good activity between pH=7.8–8.4 at 37° C. in 10 mmol/l TRIS-HCl buffer with 1.0 mmol/l DTT (dithiothreitol), 10 mmol/l $MgCl_2$ and 50 mmol/l NaCl. SgfI has a pH optimum at pH=8.2 and a temperature optimum at 37° C.

The recognition sequence and the point of cleavage was determined as follows. The recognition sequence can be partially confirmed by the complete digestion of the DNA's of Simian Virus 40 (SV40), Adenovirus-2 (Ad-2), of the phages lambda, T7 and phiX174, of the phage derivative M13mp18, and the plasmids pBR322 and PUC18. These DNA molecules are treated 16 hours with an excess of SgfI to insure complete digestion if the DNA contains the SgfI recognition site. Of the aforementioned DNA substrates, SgfI cleaves only Ad-2. The cleavage was experimentally determined to occur between 21000 bp and 22000 bp of the Ad-2 molecule which is 39437 bp in length. According to computer analysis. Only one sequence occurs within the 21000 bp and 22000 bp region of Ad-2 which is not found in any of the other aforementioned DNA substrates. A 10 bp palindromic sequence found in the 21482–21491 region of Ad-2 is where SgfI was postulated to cut. Although SgfI is known to cut in this region, it was not known whether the complete 10 bp sequence was needed or if the internal 8 bp were sufficient. Through computer analysis, the internal 8 bp sequence was not found in any of the aforementioned substrates used for SgfI digestion.

To determine whether the nucleotides at the first and tenth positions of the 10 bp sequence were needed for recognition and cleavage by SgfI, four oligonucleotide pairs representing the four possible palindromic combinations of base pairings at the first and tenth positions were synthesized. The four annealed oligonucleotides were transformed into a pGEM7Zf(+) vector having no SgfI recognition site and the cloned strand isolated and digested with SgfI. All four cloned vectors were cleaved with SgfI. Therefore, it was confirmed that base pairs at the first and tenth positions were not needed for SgfI recognition and cleavage.

To fully confirm the exact recognition of the aforementioned 8 bp sequence, the complementary pairs of oligonucleotides were synthesized and transformed into a p-GEM7Zf(+) plasmid vector not cut by SgfI. The plasmid clones comprised the three alternate sequences having palindromic substitutions at the first and eighth positions of the original 8 bp sequence found in Ad-2. SgfI did not cleave the aforementioned plasmid clones. Since the 8 bp site in Ad-2 (5'-GCGATCGC-3') is known to be hydrolyticly cleaved by SgfI, complete fidelity with the exact 8 bp sequence does exist.

The direct-incorporation protocol of fmole DNA Sequencing System (Promega Corporation) was used to characterize the SgfI cleavage site. A pGEM7Zf(+) clone containing the segment of the Ad-2 genome with the SgfI recognition site was extended using deoxynucleoside triphosphates in the dideoxy-chain-termination sequencing reaction. The products of the direct-incorporation reaction were cleaved with SgfI, and the resulting single band, when compared to the control ladder of G, A, T, C lanes indicated that DNA cleavage of Ad-2 DNA occurred in the site:

as indicated by the arrows. To determine the type of cut created, the direct-incorporation synthesis reaction cleaved with SgfI was compared to a direct-incorporation synthesis reaction carried out using a PvuI cleaved reaction. Since the internal 6 bp of the 8 bp SgfI recognition site is identical to the PvuI recognition site, PvuI can be used as a positive control in this exercise. A comparison of the single bands obtained from both the SgfI and PvuI cuts in reference to the G, A, T, C control lanes, indicated the SgfI cleavage site to be the same as that of PvuI. Therefore, SgfI and PvuI have compatible overhangs being a two base 3' overhang. The following double-stranded DNA fragments will be generated upon hydrolytic cleavage via SgfI:

5'-GCGAT...3'

3'-CGC...5' and

5'...CGC-3

3'...TAGCG-5'

SgfI is preferably isolated by culturing microorganisms of the genus Streptomyces, preferably of the species *Streptomyces griseoruber* and isolating the restriction endonuclease from the cells. *Streptomyces griseoruber* was isolated from a Florida soil sample and deposited with the American Type Culture Collection of Rockville, Md. on Aug. 3, 1993 under number ATCC 55461. Streptomyces griseoruber grow aerobically in nutrient broth 1.5% glucose medium. The optimal conditions for growth are between 28°–30° C. and at a pH between 7.0–7.4. The mass-doubling time is 8 hours.

The usual biochemical methods of purification can be used for the isolation of SgfI in which the presence of the enzyme in the respective fractions obtained can be easily tested on the basis of the cleavage of its recognition sequence. SgfI is isolated from the microorganism by the usual mechanical methods such as high pressure dispersion and sonication. Preferably, the cells of the microorganism are lysed by means of a Manton Gaulin homogenizer. Further purification of the supernatant is preferably carried out by means of precipitation, cation-exchange chromatography, and affinity chromatography. Biorex 70 TM $^{TM}$ (Bio-Rad Corp.) is suitable as the material for cation-exchange chromatography. DNA/-Sepharose is suitable as the material for affinity chromatography. Heparin-Sepharose (Scientific Protein Laboratories) is also suitable as affinity material. Other chromatographic materials such as DEAE-Sepharose and Q-Sepharose (Pharmacia) may also be employed.

SgfI can be used to cleave agarose plug genomic DNA such as Morexella bovis generating a clear and reproducible banding pattern. SgfI and the genomic DNA are mixed with a buffer solution containing $MgCl_2$ and incubated for approximately 4 hours at 37° C. The resulting DNA fragments are separated electrophoretically in agarose gels in buffer systems usually used for fragment separations in the presence of ethidium bromide.

The following examples are given for the purpose of further illustrating the invention and are not meant to be limiting.

EXAMPLE 1

*Streptomyces griseoruber* is cultured between 28°–30° C. for 48 hours and harvested at the end of the logarithmic phase. Nutrient broth 1.5% glucose is used as the culture medium. The cell paste is resuspended in 2.0 volumes TEDG (50 mmol/1 TRIS-HCl pH=7.8 at 4° C., 1 mmol/1 EDTA, 1 mmol/1 dithiothreitol, 10% vol/vol glycerol) which contains 1 mmol/1 PMSF, 2 mmol/1 benzamidine. The cell suspension is homogenized using a polytron. Subsequently the cells are lysed by passing them three times through a Manton Gaulin homogenizer at 6000 lb/inch$^2$. The nucleic acids are removed by polyethyleneimmine (PEI) precipitation. Subsequently, the centrifuged supernatant is adjusted to 40% wt/vol $NH_4Cl$ and allowed to sit for 16 hours at 4° C. The resulting pellet from the centrifugation of the $NH_4Cl$ suspension is resuspended in 200 ml of TEDG buffer. The pellet resuspension is dialyzed to a conductivity of 20 mmol/1. After dialysis, the protein mix is centrifuged to remove precipitate. Subsequently, the centrifuged supernatant is fractionated on a Biorex 70 column. A gradient of TEDG with 0–0.5 mol/1 NaCl is used for the elution. SgfI is found in the fractions between 15–0.20 mol/1 NaCl. The active fractions are equilibrated against TEDG and fractionated on a DNA/Sepharose column. A gradient of TEDG with 0–0.5 mol/1 NaCl is used for the elution. SgfI is found in the fractions between 0.13–0.18 mol/1 NaCl. The active fractions are pooled and dialyzed against a storage buffer of 10 mmol/1 TRIS-HCl, pH=7.4 (25° C.), 1 mmol/1 dithiothreitol (DTT), 50 mmol/1 NaCl mmol/1 EDTA, and 50% (vol/vol) glycerol.

EXAMPLE 2

Determination of Activity

Definition of enzyme units: 1 Unit of SgfI cleaves 1 µg Adenovirus-2 DNA within one hour at 37° C. in 50 µl final volume.

33.8 µl water and 5.2 µl Adeno-2 DNA (conc. 192 µg/ml), 4.5 µl RBC 10 X (Promega Corp.-100 mmol/1 TRIS-HCl pH=7.9, 37° C., 100 mmol/1 $MgCl_2$, 500 mmol/1 NaCl and 10 mmol/1 dithiothreitol), and .45 µl (10 mg/ml) acetylated bovine serum albumin (A-BSA) is used as the substrate mix for 5 μl of SgfI dilute to 0.2 units/μl. The solution is incubated for 1 hour at 37° C. and 10 μl of terminating reagent (25% (vol/vol) glycerol, 0.5% SDS, 50 mmol/1 EDTA, 0.2% Orange G) is added. Subsequently, a separation is carried out by electrophoresis in 0.7% agarose gels for 16 hours at 25 volts. Two bands are obtained with the endpoint called where the uppermost band, representing undigested Ad-2, is completely gone.

We claim:

1. A restriction endonuclease isolated from Streptomyces which specifically recognizes and specifically cleaves DNA comprising an octanucleotide having the sequence

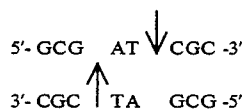

wherein said octanucleotide is cleaved at positions indicated by the arrows.

2. The restriction endonuclease of claim 1 wherein the endonuclease is isolated from *Streptomyces griseoruber*.

3. A restriction endonuclease isolated from Streptomyces which specifically recognizes the DNA sequence

and which specifically cleaves the DNA sequence at positions indicated by the arrows.

4. The restriction endonuclease of claim 3 wherein the restriction endonuclease is obtained from *Streptomyces griseoruber*.

5. The restriction endonuclease of claim 1 or 3 having a temperature optimum at 37° C. and a pH optimum of 8.2.

6. A method for isolating a restriction endonuclease having the specific recognition sequences

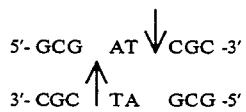

and the specific cleavage sate indicated by the arrows comprising the steps:
culturing *Streptomyces griseoruber* ATCC 55461; and isolating the endonuclease from the cells of said microorganism.

7. The method for isolating a restriction endonuclease of claim 6 wherein the step of isolating the endonuclease includes the steps of lysing the cells and isolating the cell supernatant.

8. The method for isolating a restriction endonuclease of claim 7 further including the steps of subjecting the cell supernatant to affinity chromatography and to ion-exchange chromatography.

9. The method of claim 8 wherein the the affinity chromatography is carried out using carrier-bound DNA.

10. A method for obtaining a DNA fragment with a sequence selected from the group consisting of:

5'-GCGAT ... 3'

3'-CGC ... 5' and

5'... CGC-3'

3'... TAGCG-5', the method including the steps of:
contacting a double stranded DNA molecule with a restriction endonuclease isolated from Streptomyces which specifically recognizes and specifically cleaves an octanucleotide having the sequence

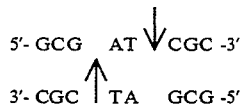

wherein said octanucleotide is cleaved at positions indicated by the arrows and under conditions favoring cleavage of the DNA molecule; and
obtaining double stranded DNA fragments therefrom.

11. A method for obtaining a restriction endonuclease which specifically recognizes and specifically cleaves the nucleotide sequence

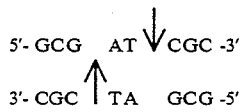

the method comprising the steps:
lysing the cells of *Streptomyces griseoruber*;
freeing the resultant lysate of cell debris; and
isolating the endonuclease from the supernatant.

12. The restriction endonuclease of claim 1 or 2 wherein the endonuclease is isolated from *Streptomyces griseoruber* ATCC 55461.

13. A method for obtaining a DNA fragment of claim 10 wherein said restriction endonuclease is obtained from *Streptomyces griseoruber* ATCC 55461.

* * * * *

UNITED STATES PATENT AND TRADEMARK OFFICE
CERTIFICATE OF CORRECTION

PATENT NO. : 5,391,487

DATED : February 21, 1995

INVENTOR(S) : James R. Kappelman, Raymond J. Williams, Elizabeth E. Murray and Nadia I. Vesselinova It is certified that error appears in the above-indentified patent and that said Letters Patent is hereby corrected as shown below:

Column 4, line 5, delete the first occurrence of "TM" after "70".

Column 4, line 49, "15-0.20" should be -- 0.15-0.20 --

Column 4, line 56, after "NaCl" insert -- , 0.1 --

Column 6, line 7, delete the first occurrence of "the" after "wherein".

Signed and Sealed this

Twenty-third Day of May, 1995

Attest:

BRUCE LEHMAN

Attesting Officer       Commissioner of Patents and Trademarks